United States Patent
Ewer et al.

(10) Patent No.: US 10,945,859 B2
(45) Date of Patent: Mar. 16, 2021

(54) EXPANDING FUSION CAGES

(71) Applicant: IMDS LLC, Providence, UT (US)

(72) Inventors: Darin Ewer, Providence, UT (US);
Trevor K. Lewis, Lehi, UT (US);
Justin Hyer, Hyrum, UT (US);
Nicholas Slater, Chandler, AZ (US);
Nathan O. Plowman, Wellsville, UT (US)

(73) Assignee: AMPLIFY SURGICAL, INC., Laguna Hills, CA (US)

( * ) Notice: Subject to any disclaimer, the term of this patent is extended or adjusted under 35 U.S.C. 154(b) by 0 days.

(21) Appl. No.: 16/261,383

(22) Filed: Jan. 29, 2019

(65) Prior Publication Data

US 2019/0231548 A1    Aug. 1, 2019

Related U.S. Application Data

(60) Provisional application No. 62/623,278, filed on Jan. 29, 2018.

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2002/3055* (2013.01); *A61F 2002/30148* (2013.01); *A61F 2002/30154* (2013.01); *A61F 2002/30265* (2013.01); *A61F 2002/30556* (2013.01); *A61F 2002/30579* (2013.01); *A61F 2002/30593* (2013.01); *A61F 2002/30622* (2013.01); *A61F 2002/30828* (2013.01)

(58) Field of Classification Search
CPC .................. A61F 2/447; A61F 2/4611; A61F 2002/30148; A61F 2002/30154; A61F 2002/30265; A61F 2002/3055; A61F 2002/30556; A61F 2002/30279; A61F 2002/30593; A61F 2002/30622; A61F 2002/30828
USPC ....................................... 623/17.11
See application file for complete search history.

(56) References Cited

U.S. PATENT DOCUMENTS

| | | |
|---|---|---|
| 4,164,225 A | 8/1979 | Johnson |
| 4,657,550 A | 4/1987 | Daher |
| 4,834,757 A | 5/1989 | Brantigan |
| 4,863,476 A | 9/1989 | Shepperd |
| 5,059,193 A | 10/1991 | Kuslich |
| 5,171,278 A | 12/1992 | Pisharodi |
| 5,290,312 A | 3/1994 | Kojimoto |
| 5,306,310 A | 4/1994 | Siebels |
| 5,336,223 A | 8/1994 | Rogers |
| 5,390,683 A | 2/1995 | Pisharodi |
| 5,405,391 A | 4/1995 | Hednerson |

(Continued)

FOREIGN PATENT DOCUMENTS

| | | |
|---|---|---|
| AU | 2013206287 A1 | 7/2013 |
| AU | 2013262504 B2 | 4/2017 |

(Continued)

*Primary Examiner* — Eduardo C Robert
*Assistant Examiner* — David C Comstock
(74) *Attorney, Agent, or Firm* — Maywood IP Law; David Meibos

(57) ABSTRACT

Expandable fusion cages are disclosed which may be expandable in two substantially mutually perpendicular directions.

18 Claims, 10 Drawing Sheets

(56) References Cited

U.S. PATENT DOCUMENTS

| | | |
|---|---|---|
| 5,425,772 A | 6/1995 | Brantigan |
| 5,443,514 A | 8/1995 | Steffee |
| 5,458,641 A | 10/1995 | Ramirez Jimenez |
| 5,554,191 A | 9/1996 | Lahille |
| 5,571,192 A | 11/1996 | Schonhoffer |
| 5,653,762 A | 8/1997 | Pisharodi |
| 5,653,763 A | 8/1997 | Errico |
| 5,658,335 A | 8/1997 | Allen |
| 5,665,122 A | 9/1997 | Kambin |
| 5,693,100 A | 12/1997 | Pisharodi |
| 5,702,455 A | 12/1997 | Saggar |
| 5,716,415 A | 2/1998 | Steffee |
| 5,776,198 A | 7/1998 | Rabbe |
| 5,782,832 A | 7/1998 | Larsen |
| 5,865,848 A | 2/1999 | Baker |
| 5,980,522 A | 11/1999 | Koros |
| 5,989,290 A | 11/1999 | Biedermann |
| 6,015,436 A | 1/2000 | Schonhoffer |
| 6,039,761 A | 3/2000 | Li |
| 6,045,579 A | 4/2000 | Hochshuler |
| 6,080,193 A | 6/2000 | Hochshuler |
| 6,093,207 A | 7/2000 | Pisharodi |
| 6,102,950 A | 8/2000 | Vaccaro |
| 6,117,174 A | 9/2000 | Nolan |
| 6,126,689 A | 10/2000 | Brett |
| 6,126,869 A | 10/2000 | Haaland |
| 6,129,763 A | 10/2000 | Chauvin |
| 6,159,244 A | 12/2000 | Suddaby |
| 6,174,334 B1 | 1/2001 | Suddaby |
| 6,176,881 B1 | 1/2001 | Schar et al. |
| 6,183,517 B1 | 2/2001 | Suddaby |
| 6,190,413 B1 | 2/2001 | Sutcliffe |
| 6,190,414 B1 | 2/2001 | Young |
| 6,193,755 B1 | 2/2001 | Metz Stavenhagen |
| 6,193,756 B1 | 2/2001 | Studer |
| 6,193,757 B1 | 2/2001 | Foley |
| 6,200,348 B1 | 3/2001 | Biedermann |
| 6,214,050 B1 | 4/2001 | Huene |
| 6,296,647 B1 | 10/2001 | Robioneck |
| 6,299,644 B1 | 10/2001 | Vanderschot |
| 6,332,895 B1 | 12/2001 | Suddaby |
| 6,395,034 B1 | 5/2002 | Suddaby |
| 6,413,278 B1 | 7/2002 | Marchosky |
| 6,419,705 B1 | 7/2002 | Erickson |
| 6,436,140 B1 | 8/2002 | Liu |
| 6,454,806 B1 | 9/2002 | Cohen |
| 6,491,724 B1 | 12/2002 | Ferree |
| 6,562,074 B2 | 5/2003 | Gerbec |
| 6,582,431 B1 | 6/2003 | Ray |
| 6,648,917 B2 | 11/2003 | Gerbec |
| 6,660,038 B2 | 12/2003 | Boyer, II |
| 6,666,891 B2 | 12/2003 | Boehm, Jr. |
| 6,685,742 B1 | 2/2004 | Jackson |
| 6,706,070 B1 | 3/2004 | Wagner |
| 6,709,458 B2 | 3/2004 | Michelson |
| 6,723,126 B1 | 4/2004 | Berry |
| 6,730,126 B2 | 5/2004 | Boehm, Jr. |
| 6,746,484 B1 | 6/2004 | Liu |
| 6,833,006 B2 | 12/2004 | Foley |
| 6,852,129 B2 | 2/2005 | Gerbec |
| 6,863,673 B2 | 3/2005 | Gerbec |
| 6,893,464 B2 | 5/2005 | Kiester |
| 7,070,598 B2 | 7/2006 | Lim |
| 7,513,900 B2 | 4/2009 | Carrison |
| 7,625,377 B2 | 12/2009 | Veldhuizen |
| 7,799,081 B2 | 9/2010 | McKinley |
| 7,824,427 B2 | 11/2010 | Perez-Cruet |
| 7,846,206 B2 | 12/2010 | Oglaza |
| 7,879,098 B1 | 2/2011 | Simmons, Jr. |
| 7,922,729 B2 | 4/2011 | Michelson |
| 8,012,207 B2 | 9/2011 | Kim |
| 8,097,018 B2 | 1/2012 | Malandain |
| 8,097,035 B2 | 1/2012 | Glenn |
| 8,109,972 B2 | 2/2012 | Zucherman |
| 8,110,004 B2 | 2/2012 | Valdevit |
| 8,152,837 B2 | 4/2012 | Altarac |
| 8,317,798 B2 | 11/2012 | Lim |
| 8,323,344 B2 | 12/2012 | Galley |
| 8,409,291 B2 | 4/2013 | Blackwell |
| 8,491,657 B2 | 7/2013 | Attia |
| 8,496,709 B2 | 7/2013 | Schell |
| 8,506,635 B2 | 8/2013 | Palmatier |
| 8,541,355 B2 | 9/2013 | Fleckenstein |
| 8,568,481 B2 | 10/2013 | Olmos |
| 8,579,907 B2 | 11/2013 | Lim |
| 8,628,576 B2 | 1/2014 | Triplett |
| 8,652,174 B2 | 2/2014 | Gabelberger |
| 8,663,329 B2 | 3/2014 | Ernst |
| 8,678,576 B2 | 3/2014 | Edombingo |
| 8,685,095 B2 | 4/2014 | Miller |
| 8,777,993 B2 | 7/2014 | Siegal |
| 8,778,027 B2 | 7/2014 | Medina |
| 8,808,385 B1 | 8/2014 | Smith |
| 8,900,305 B2 | 12/2014 | Stad |
| 8,926,704 B2 | 1/2015 | Glerum |
| 8,940,048 B2 | 1/2015 | Butler |
| 9,060,876 B1 | 6/2015 | To |
| 9,308,099 B2 | 4/2016 | Triplett |
| 9,445,918 B1 | 9/2016 | Lin |
| 9,913,727 B2 * | 3/2018 | Thommen ............... A61F 2/447 |
| 10,105,238 B2 | 10/2018 | Koch |
| 10,201,431 B2 | 2/2019 | Slater |
| 2001/0032017 A1 | 10/2001 | Alfaro |
| 2002/0010511 A1 | 1/2002 | Michelson |
| 2003/0229355 A1 | 12/2003 | Keller |
| 2004/0002758 A1 | 1/2004 | Landry |
| 2004/0034430 A1 | 2/2004 | Falahee |
| 2005/0177235 A1 | 8/2005 | Baynham |
| 2005/0182416 A1 | 8/2005 | Lim |
| 2005/0222681 A1 | 10/2005 | Richley |
| 2005/0234555 A1 | 10/2005 | Sutton |
| 2005/0278036 A1 | 12/2005 | Leonard |
| 2006/0142858 A1 | 6/2006 | Colleran |
| 2006/0167547 A1 | 7/2006 | Suddaby |
| 2007/0043440 A1 | 2/2007 | William |
| 2007/0049935 A1 | 3/2007 | Edidin |
| 2007/0067034 A1 | 3/2007 | Chirico |
| 2007/0118222 A1 | 5/2007 | Lang |
| 2007/0198089 A1 | 8/2007 | Moskowitz |
| 2007/0219634 A1 | 9/2007 | Greenhalgh |
| 2007/0260315 A1 | 11/2007 | Foley |
| 2007/0282449 A1 | 12/2007 | de Villiers |
| 2008/0033440 A1 | 2/2008 | Moskowitz |
| 2008/0045968 A1 | 2/2008 | Yu |
| 2008/0082167 A1 | 4/2008 | Edidin |
| 2008/0108990 A1 | 5/2008 | Mitchell |
| 2008/0114367 A1 | 5/2008 | Meyer |
| 2008/0167657 A1 | 7/2008 | Greenhalgh |
| 2008/0183204 A1 | 7/2008 | Greenhalgh |
| 2008/0195152 A1 | 8/2008 | Altarac |
| 2008/0219604 A1 | 9/2008 | Chen |
| 2008/0221686 A1 | 9/2008 | Ferree |
| 2008/0243255 A1 | 10/2008 | Butler |
| 2008/0249604 A1 | 10/2008 | Donovan |
| 2008/0281346 A1 | 11/2008 | Greenhalgh |
| 2008/0288072 A1 | 11/2008 | Kohm |
| 2008/0288078 A1 | 11/2008 | Kohm |
| 2008/0319549 A1 | 12/2008 | Greenhalgh |
| 2009/0076607 A1 | 3/2009 | Aalsma |
| 2009/0157084 A1 | 6/2009 | Aalsma |
| 2009/0198338 A1 | 8/2009 | Phan |
| 2009/0222093 A1 | 9/2009 | Liu |
| 2009/0222100 A1 | 9/2009 | Cipoletti |
| 2009/0281628 A1 | 11/2009 | Oglaza |
| 2010/0082109 A1 | 4/2010 | Greenhalgh |
| 2010/0185291 A1 | 7/2010 | Jimenez |
| 2010/0249720 A1 | 9/2010 | Biyani |
| 2010/0286783 A1 | 11/2010 | Lechmann |
| 2010/0305705 A1 | 12/2010 | Butler |
| 2010/0318127 A1 | 12/2010 | Phan |
| 2011/0004307 A1 | 1/2011 | Ahn |
| 2011/0125270 A1 | 5/2011 | Paul |
| 2011/0172774 A1 | 7/2011 | Varela |
| 2011/0270396 A1 | 11/2011 | Leibowitz |

(56) References Cited

U.S. PATENT DOCUMENTS

| | | | |
|---|---|---|---|
| 2011/0276141 A1 | 11/2011 | Caratsch | |
| 2011/0282453 A1 | 11/2011 | Greenhalgh | |
| 2011/0319997 A1 | 12/2011 | Glerum | |
| 2012/0004732 A1 | 1/2012 | Goel | |
| 2012/0053642 A1 | 3/2012 | Lozier | |
| 2012/0071977 A1 | 3/2012 | Oglaza | |
| 2012/0083887 A1 | 4/2012 | Purcell | |
| 2012/0083889 A1 | 4/2012 | Purcell | |
| 2012/0123546 A1 | 5/2012 | Medina | |
| 2012/0136442 A1 | 5/2012 | Kleiner | |
| 2012/0150241 A1 | 6/2012 | Ragab | |
| 2012/0185045 A1 | 7/2012 | Morris | |
| 2012/0185047 A1 | 7/2012 | Wooley | |
| 2012/0185049 A1 | 7/2012 | Varela | |
| 2012/0209386 A1* | 8/2012 | Triplett | A61F 2/447 623/17.16 |
| 2012/0215313 A1 | 8/2012 | Saidha | |
| 2012/0215316 A1 | 8/2012 | Mohr | |
| 2012/0226357 A1 | 9/2012 | Varela | |
| 2012/0245691 A1 | 9/2012 | Reimels | |
| 2012/0259416 A1* | 10/2012 | Blackwell | A61F 2/4455 623/17.16 |
| 2013/0079882 A1 | 3/2013 | Wolfe | |
| 2013/0079883 A1 | 3/2013 | Butler | |
| 2013/0144391 A1 | 6/2013 | Siegal | |
| 2013/0158669 A1 | 6/2013 | Sungarian | |
| 2013/0190876 A1 | 7/2013 | Drochner | |
| 2013/0297029 A1* | 11/2013 | Kana | A61F 2/4455 623/17.16 |
| 2013/0310939 A1 | 11/2013 | Fabian | |
| 2013/0325128 A1 | 12/2013 | Perloff | |
| 2014/0031940 A1 | 1/2014 | Banouskou | |
| 2014/0039622 A1 | 2/2014 | Glerum | |
| 2014/0052253 A1 | 2/2014 | Perloff | |
| 2014/0088714 A1 | 3/2014 | Miller | |
| 2014/0121774 A1 | 5/2014 | Glerum | |
| 2014/0128977 A1 | 5/2014 | Glerum | |
| 2014/0172106 A1 | 6/2014 | To | |
| 2014/0188224 A1 | 7/2014 | Dmuschewsky | |
| 2014/0194991 A1 | 7/2014 | Jimenez | |
| 2014/0194992 A1 | 7/2014 | Medina | |
| 2014/0257484 A1 | 9/2014 | Flower | |
| 2014/0277490 A1* | 9/2014 | Perloff | A61F 2/442 623/17.16 |
| 2014/0379086 A1 | 12/2014 | Elahinia | |
| 2015/0012098 A1 | 1/2015 | Eastlack | |
| 2015/0018951 A1 | 1/2015 | Loebl | |
| 2015/0073552 A1 | 3/2015 | To | |
| 2015/0257894 A1* | 9/2015 | Levy | A61F 2/4611 623/17.15 |
| 2015/0351923 A1* | 12/2015 | Emstad | A61F 2/4611 623/17.16 |
| 2015/0351928 A1* | 12/2015 | Butler | A61F 2/4611 623/17.16 |
| 2017/0056200 A1* | 3/2017 | Koch | A61F 2/44 |
| 2018/0110629 A1 | 4/2018 | Ewer | |
| 2018/0344476 A1 | 12/2018 | Koch | |
| 2020/0205992 A1* | 7/2020 | Bernard | A61F 2/30771 |

FOREIGN PATENT DOCUMENTS

| | | |
|---|---|---|
| CA | 2567274 C | 11/2014 |
| CN | 202458786 | 10/2012 |
| EP | 0260044 A1 | 3/1988 |
| EP | 1006956 A1 | 6/2000 |
| EP | 2793760 A1 | 10/2014 |
| EP | 3038566 A1 | 7/2016 |
| EP | 2729092 B1 | 9/2016 |
| EP | 2693989 B1 | 9/2017 |
| EP | 3340938 A1 | 7/2018 |
| WO | WO1998034568 A1 | 8/1998 |
| WO | WO2000025706 A1 | 5/2000 |
| WO | WO2002076335 A2 | 10/2002 |
| WO | WO2003032812 A2 | 4/2003 |
| WO | WO2005112834 A2 | 12/2005 |
| WO | WO2008070863 A2 | 6/2008 |
| WO | WO2009037509 A1 | 3/2009 |
| WO | WO2009092102 A1 | 7/2009 |
| WO | WO2010078468 A2 | 7/2010 |
| WO | WO2010105181 A1 | 9/2010 |
| WO | WO2012047712 A1 | 4/2012 |
| WO | WO2012112596 A1 | 8/2012 |
| WO | WO2012141715 A1 | 10/2012 |
| WO | WO2013052807 A2 | 4/2013 |
| WO | WO2013109346 A1 | 7/2013 |
| WO | WO2013173767 A1 | 11/2013 |
| WO | WO2014144696 A1 | 9/2014 |
| WO | WO2014151162 A1 | 9/2014 |
| WO | WO2014164625 A1 | 10/2014 |
| WO | WO2015009998 A1 | 1/2015 |
| WO | WO2015031291 A1 | 3/2015 |
| WO | WO2015063719 A1 | 5/2015 |
| WO | WO2017035155 A1 | 3/2017 |
| WO | WO2018081322 A1 | 5/2018 |

* cited by examiner

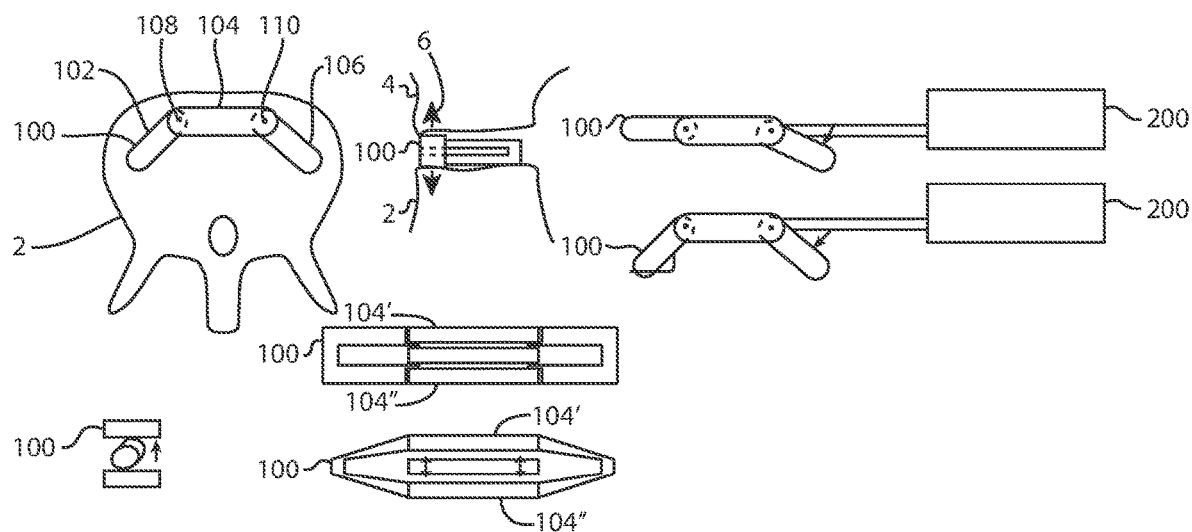
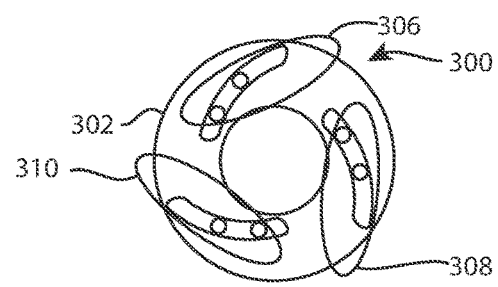
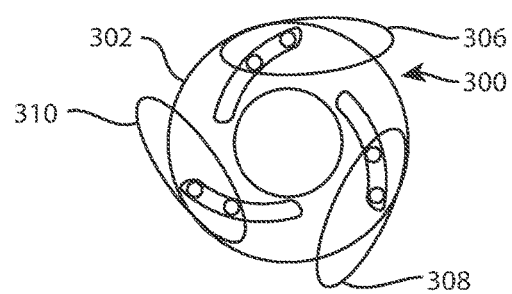
FIG. 1
FIG. 2

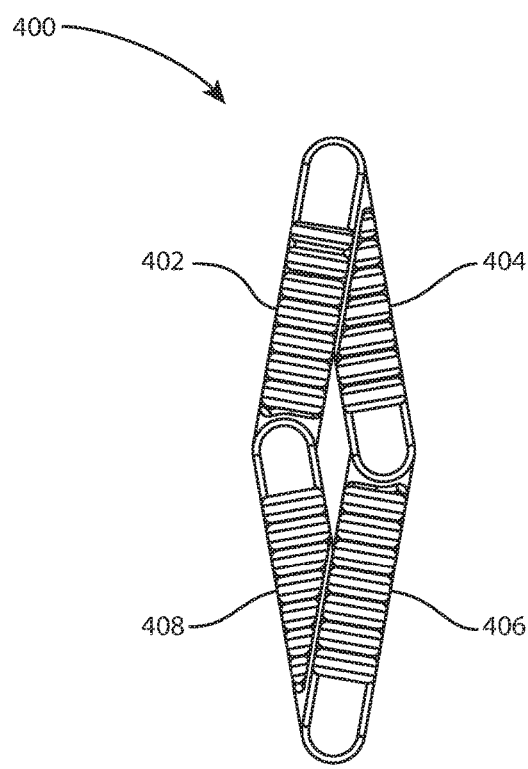
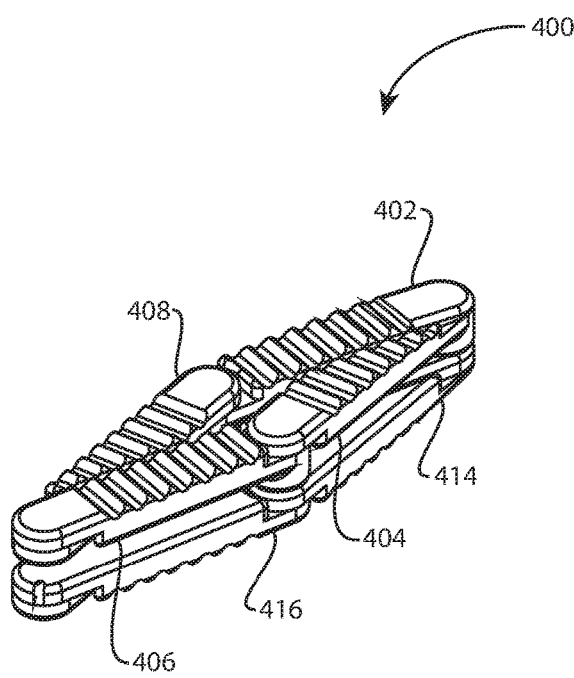
FIG. 4A  FIG. 4B
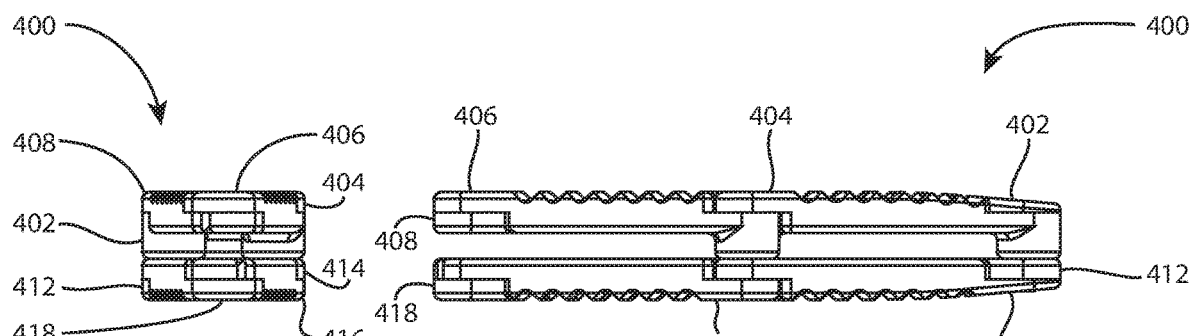
FIG. 4C  FIG. 4D

EXPANDING FUSION CAGES

CROSS-REFERENCE TO RELATED APPLICATIONS

The present application claims the benefit of U.S. Provisional Application Ser. No. 62/623,278, filed on Jan. 29, 2018 entitled "Expanding Fusion Cages". The foregoing is incorporated by reference as though set forth herein in its entirety.

TECHNICAL FIELD

The present disclosure relates to expanding fusion cages for use between bones or bone fragments. More specifically, the present disclosure relates to intervertebral fusion cages that are expandable in the transverse plane and along the cephalad-caudal axis.

BACKGROUND

Fusion cages may be inserted between bones or bone fragments to stabilize the bones or bone fragments relative to each other so that fusion may occur. It is desirable for the fusion cages to be movable between an insertion configuration and a final implanted configuration which is larger in at least one direction or dimension (length, width, height) than the insertion configuration. It is desirable for the insertion configuration to be small, at least in the width and/or height dimensions, transverse to the insertion trajectory, so that the fusion cage may be inserted into its implantation site through a small opening, incision, portal, cannula, or the like, so as to minimize surgical trauma to the patient due to creating a surgical exposure to the implantation site. It is desirable for the final implanted configuration to be larger in at least one direction or dimension, such as the width and/or height dimensions transverse to the insertion trajectory, so that the fusion cage may be expanded to fill the anatomical space between the bones or bone fragments, thus tensioning the surrounding soft tissues to stabilize the bones or bone fragments.

The insertion configuration may be referred to as a collapsed configuration and the final implanted configuration may be referred to as an expanded configuration. The expanded configuration may be a partially or fully expanded configuration. The fusion cages disclosed herein move between the insertion or collapsed configuration and the final implanted or expanded configuration.

The fusion cages may move through one or more intermediate configurations as they move between the insertion or collapsed configuration and the final implanted or expanded configuration.

For example, in the context of an intervertebral fusion cage, one intermediate configuration may be a laterally expanded configuration in which the fusion cage expands in the transverse plane. Another intermediate configuration may be a vertically expanded configuration in which the fusion cage expands along the cephalad-caudal axis. In this context, the final implanted or expanded configuration may be a laterally and/or vertically expanded configuration.

SUMMARY OF THE INVENTION

The various systems and methods of the present invention have been developed in response to the present state of the art, and in particular, in response to the problems and needs in the art that have not yet been fully solved by currently available expandable fusion cage system. The systems and methods of the present invention may provide a preferred expandable fusion cage system.

To achieve the foregoing, and in accordance with the invention as embodied and broadly described herein, in an aspect of the technology, an expandable fusion cage system comprising a first link extending between a first end and an opposite second end; a second link extending between a first end and an opposite second end, the second link comprising a plane extending between the first and second ends and an axis extending normal to the plane; and a third link extending between a first end and an opposite second end; a center cam extending through the second link, between the first and second end; wherein the first ends of the first and second links are hinged together and the second ends of the second and third links are hinged together, so that the first and third links are rotatable relative to the second link in the plane; wherein the first link comprises a first upper member and a first lower member, wherein at the second end of the first link, the first upper member is a first fixed distance from the first lower member along the axis; wherein the second link comprises a second upper member and a second lower member, wherein the second upper member is movable relative to the second lower member along the axis; wherein the third link comprises a third upper member and a third lower member wherein at the first end of the third link, the third upper member is a second fixed distance from the third lower member along the axis.

Another advantage of the present disclosure is an expandable fusion cage system comprising an upper body having an outer perimeter; a lower body having an outer perimeter and movably coupled to the upper body for movement along an axis that extends between the upper and lower bodies; and a lateral element movably coupled to the upper body for movement in a plane that is perpendicular to the axis, wherein the lateral element is movable between a first position and a second position, wherein in the first position, more than half of the lateral element is recessed within the outer perimeters of the upper and lower bodies when viewed along the axis, wherein in the second position, the lateral element protrudes outwardly beyond the outer perimeters of the upper and lower bodies when viewed along the axis.

A further embodiment of the disclosure is an expandable fusion cage system comprising a cage comprising a plurality of links hinged together end to end, wherein the links are rotatable relative to each other in a plane; a wedge component having a tapered first end; and wherein each one of the plurality of links comprises an upper member and a lower member, wherein the upper members are movable relative to the lower members along an axis normal to the plane; and wherein the wedge component is receivable between the upper and lower members.

These and other features and advantages of the present invention will become more fully apparent from the following description and appended claims, or may be learned by the practice of the invention as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 1 is a schematic drawing of an expanding fusion cage, with and without an inserter instrument;

FIG. 2 is a schematic drawing of another expanding fusion cage;

FIG. 4A is a top view of the fusion cage of FIG. 3A in the insertion configuration; FIG. 4B is an isometric view of the fusion cage of FIG. 4A; FIG. 4C is a front view of the fusion cage of FIG. 4A; and FIG. 4D is a side view of the fusion cage of FIG. 4A;

DETAILED DESCRIPTION

Figure 3A:
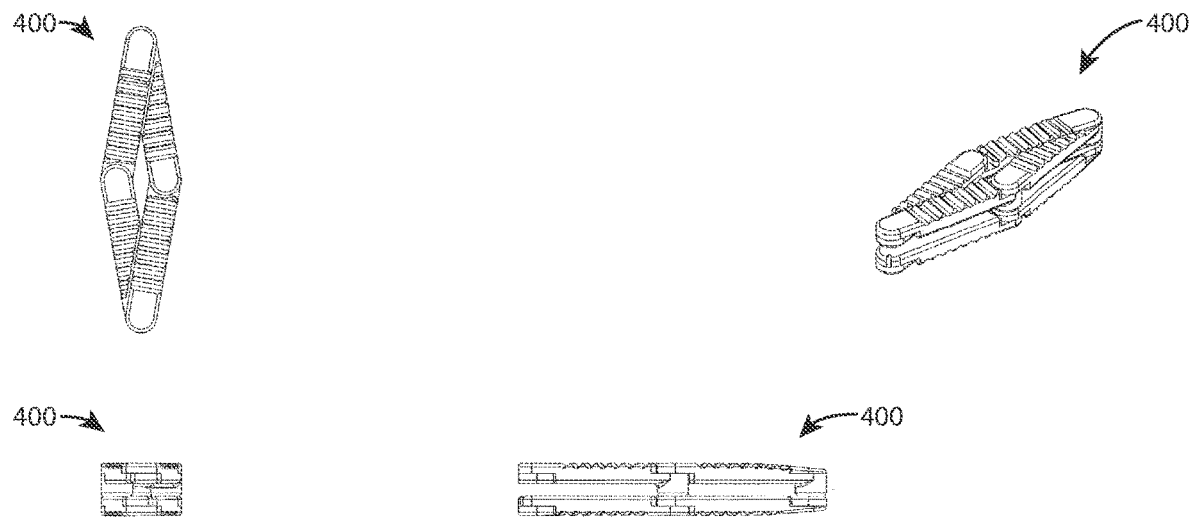
FIG. 3A includes top, isometric, front, and side views of yet another expanding fusion cage in an insertion configuration.
Figure 3B:
FIG. 3B includes top, isometric, front, and side views of the fusion cage of FIG. 3A in a laterally expanded configuration.
Figure 3C:
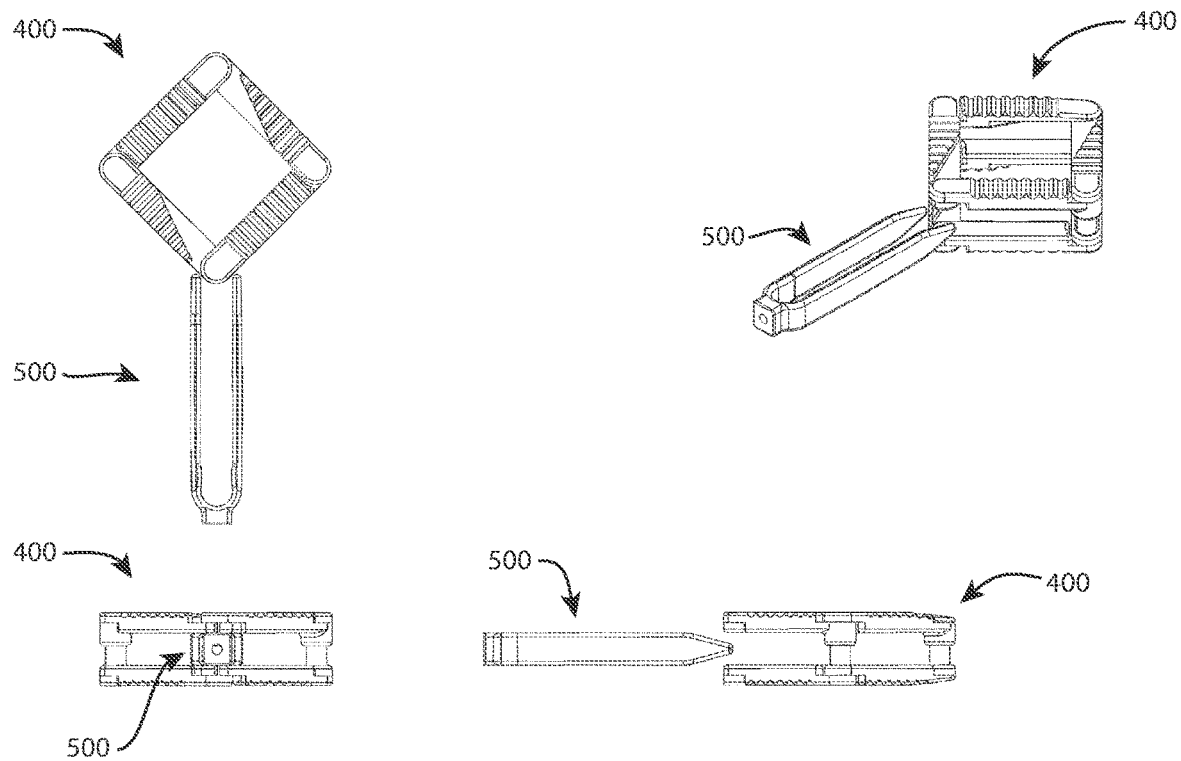
FIG. 3C includes top, isometric, front, and side views of the fusion cage of FIG. 3B in a laterally and vertically expanded configuration, including a wedge or spreading clip.
Figure 3D:
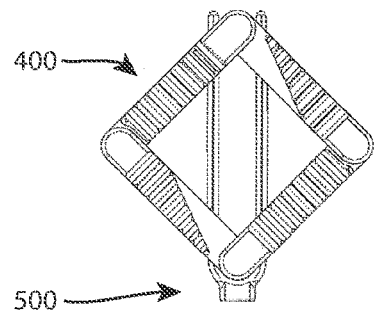
FIG. 3D includes top, front, and side views of the fusion cage of FIG. 3C in a final implanted configuration with the wedge or spreading clip installed.
Figure 3D:
Figure 5A:
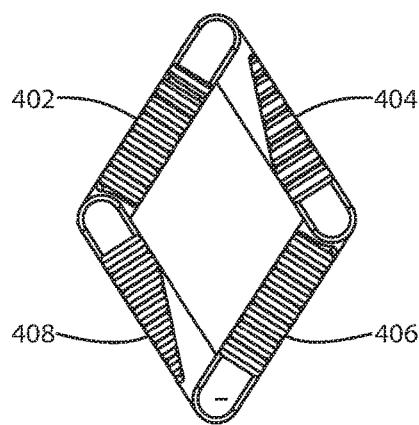
FIG. 5A is a top view of the fusion cage of FIG. 3B in the laterally expanded configuration.
Figure 5B:
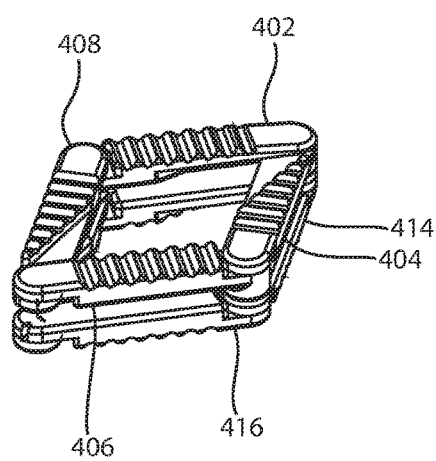
FIG. 5B is an isometric view of the fusion cage of FIG. 5A.
Figure 5C:
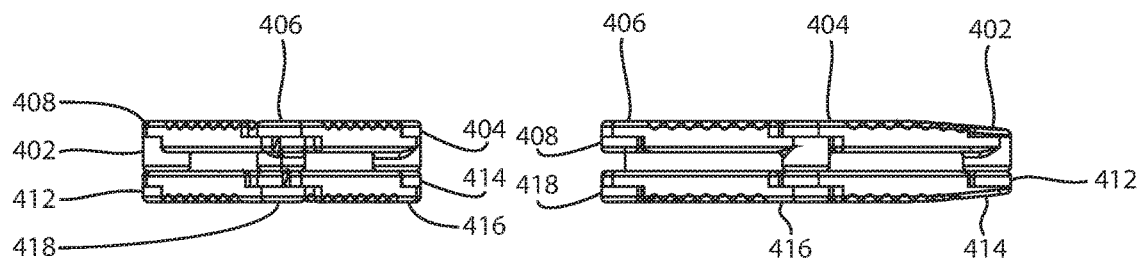
FIG. 5C is a front view of the fusion cage of FIG. 5A.
Figure 5D:
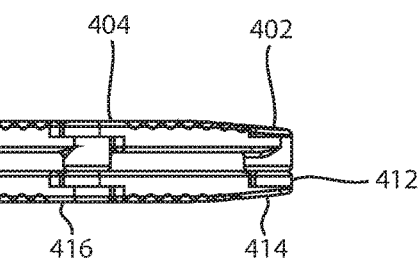
FIG. 5D is a side view of the fusion cage of FIG. 5A.
Figure 6A:
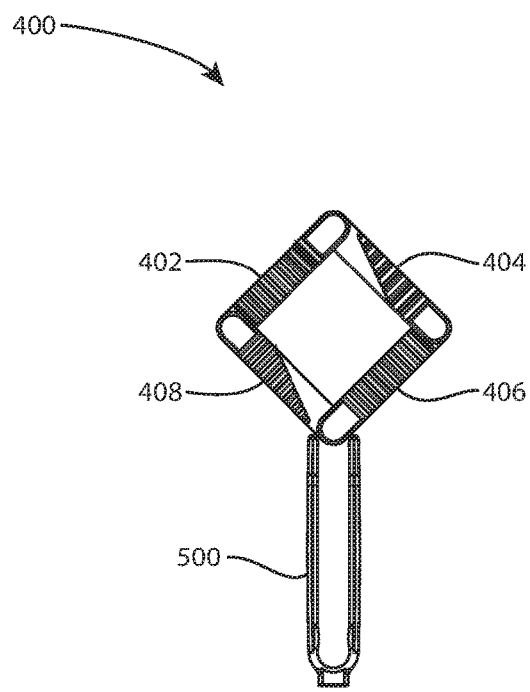
FIG. 6A is a top view of the fusion cage and wedge of FIG. 3C in the laterally and vertically expanded configuration.
Figure 6B:
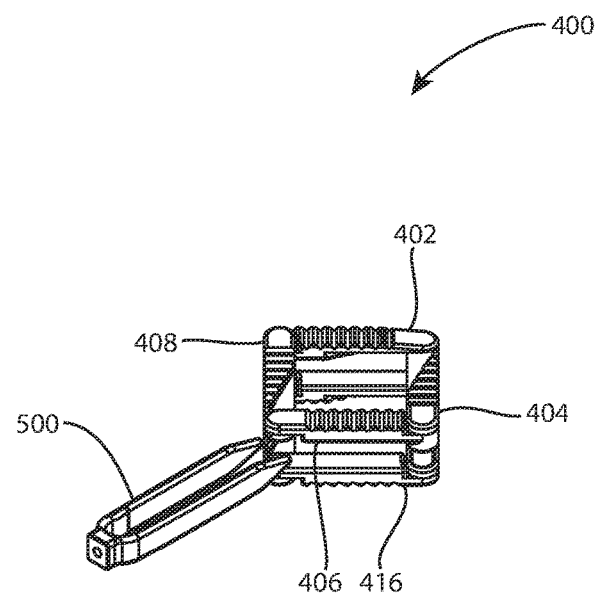
FIG. 6B is an isometric view of the fusion cage and wedge of FIG. 6A.
Figure 6C:
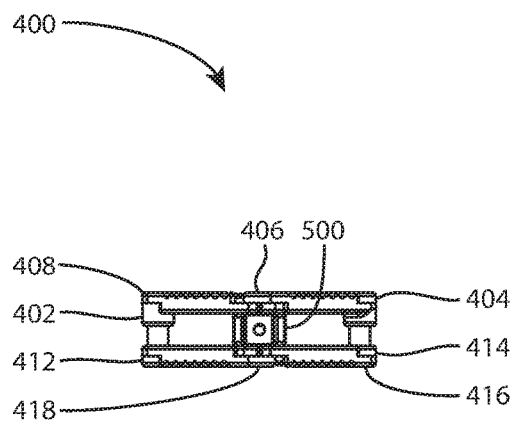
FIG. 6C is a front view of the fusion cage and wedge of FIG. 6A.
Figure 6D:
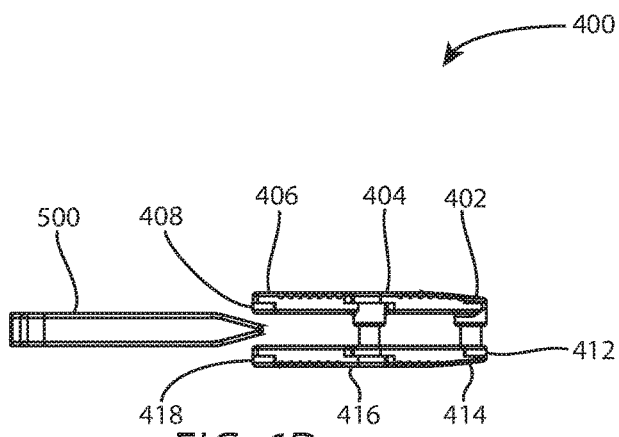
FIG. 6D is a side view of the fusion cage and wedge of FIG. 6A.
Figure 7A:
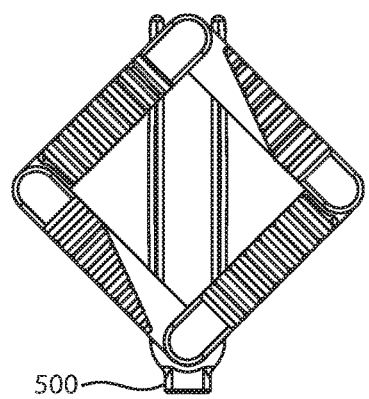
FIG. 7A is a top view of the fusion cage and wedge of FIG. 3D in the final implanted configuration.
Figure 7B:
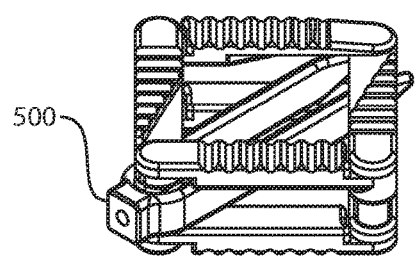
FIG. 7B is an isometric view of the fusion cage and wedge of FIG. 7A.
Figure 7C:
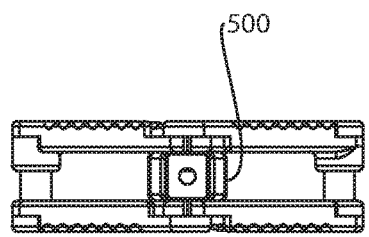
FIG. 7C is a front view of the fusion cage and wedge of FIG. 7A.
Figure 7D:
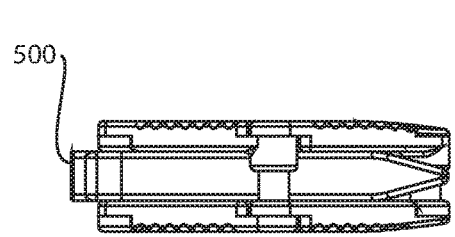
FIG. 7D is a side view of the fusion cage and wedge of FIG. 7A.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. A sagittal plane divides a body into right and left portions. A mid-sagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior or cephalad means toward the head. Inferior means toward the feet. Caudal means toward the tail/coccyx. A cephalad-caudal axis is a vertical axis which extends along the central midline axis of the vertebral bodies of the spine. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. Proximal means located toward a center of a body, or toward a user. Distal means located away from the center of the body, or away from a user. These descriptive terms may be applied to an animate or inanimate body.

Standard spinal descriptive terminology is used herein with the ordinary and customary meanings.

Referring to FIG. 1, an expanding fusion cage 100, inserter instrument 200, lower vertebra 2, and upper vertebra 4 are shown.

The expanding fusion cage 100 may include a first link 102, a second link 104, and a third link 106. The first and second links may be hinged together at a first hinge 108 and the second and third links may be hinged together at a second hinge 110. The first, second, and third links may be movable relative to each other about the first and second hinges in the transverse plane for lateral expansion. The first, second, and third links may each be divided into an upper link, for example upper second link 104', and a lower link, for example lower second link 104". Each pair of upper and lower links may be movable relative to each other along the cephalad-caudal axis 6 for vertical expansion. The free ends of the first and third links may have a fixed height along the cephalad-caudal axis so that vertical expansion occurs mainly in the vicinity of the second link 104.

The inserter instrument 200 may include a shaft with a distal end that removably couples to the fusion cage 100. The illustrated inserter instrument 200 couples to a proximal end of the second link 104 near the second hinge 110, and may extend along the second link 104 to the first hinge 108. The inserter instrument 200 may be actuated to cause lateral and vertical expansion of the fusion cage 100. Lateral and vertical expansion may occur as separate steps, as seamlessly sequential steps, or simultaneously. Lateral expansion may occur before vertical expansion, or vice versa.

Alternatively, as noted and shown in the lower left region of FIG. 1, a cam on a screw may drive vertical expansion. The screw is shown along the centerline of the implant. The screw rotates a cam which provides vertical motion to separate the upper and lower sections of the implant.

Referring to FIG. 2, another expanding fusion cage 300 is shown. Fusion cage 300 may operate according to the principles of a reverse iris. Fusion cage 300 may include an upper ring 302, a lower ring 304, and at least one lateral element 306. In the example shown, three lateral elements 306, 308, 310 are shown. The lateral elements may be connected to the rings via complementary dovetail features. The lateral elements may be movable between an insertion configuration, in which the lateral elements are mostly or entirely recessed within the outer perimeter of the rings, and a laterally expanded configuration, in which the lateral elements protrude outwardly beyond the outer perimeter of the rings. The upper and lower rings may be movable between an insertion configuration, in which the rings are close together, and a vertically expanded configuration, in which the rings are spaced farther apart. The fusion cage 300 may have a final implanted configuration after lateral and vertical expansion.

Referring to FIGS. 3A-8B, yet another expanding fusion cage 400 and wedge or spreading clip 500 are shown. The wedge 500 may be considered a component part of the fusion cage 400, or the fusion cage 400 and wedge 500 may be considered to form an implant system.

Figure 8A:
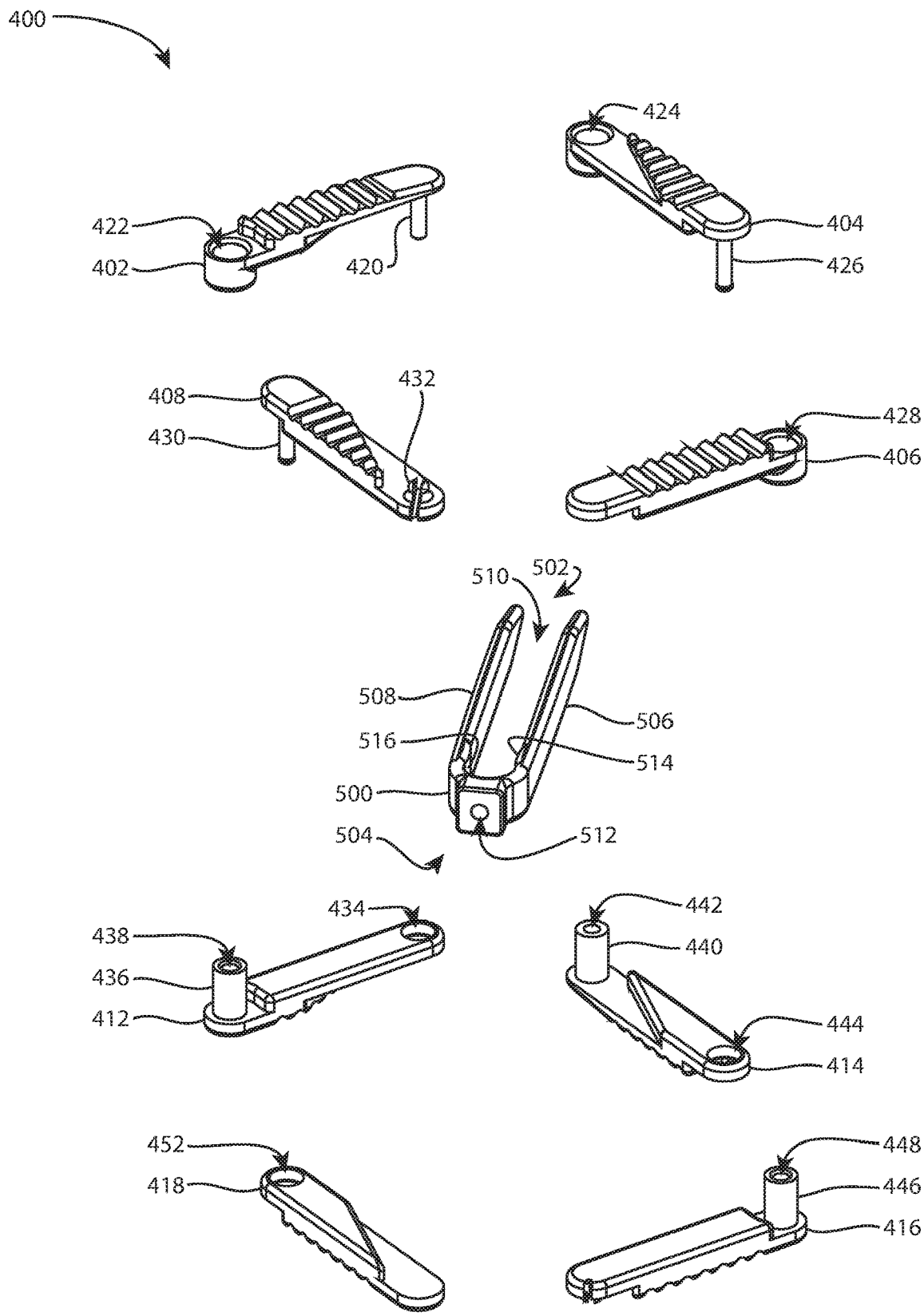
FIG. 8A is an exploded perspective view of the fusion cage and wedge of FIG. 7A.
Figure 8B:
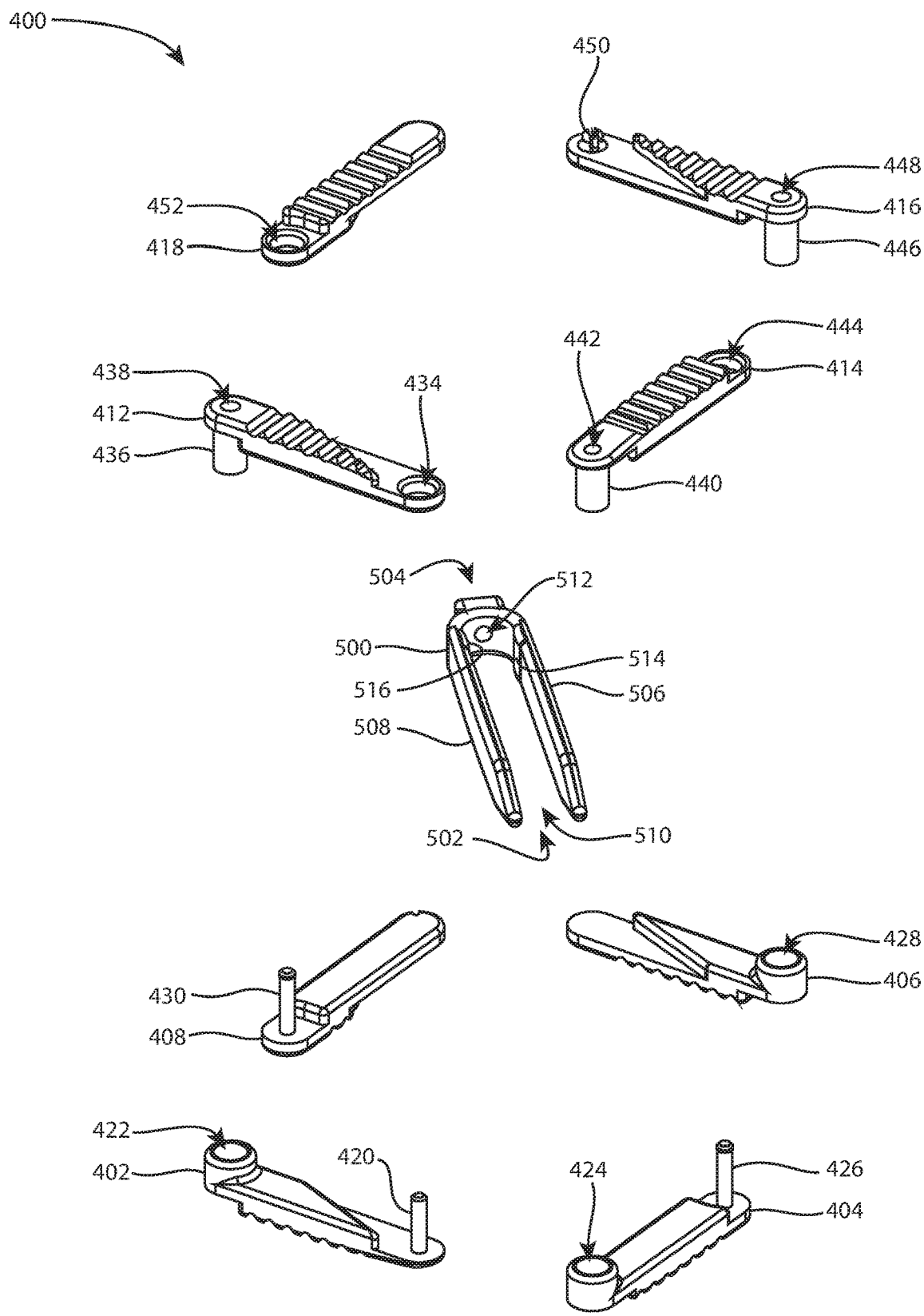
FIG. 8B is another exploded perspective view of the fusion cage and wedge of FIG. 7A from a different direction.

The fusion cage 400 may include four upper links 402, 404, 406, 408 and four lower links 412, 414, 416, 418. The four upper links may be hinged together end to end to form a quadrilateral polygon with four sides and four vertices or corners. The four lower links may also be hinged together to form a quadrilateral. Any number of upper and lower links may be present. For example, there may be five upper or lower links, forming a pentagon, or eight links forming an octagon. There may be a different number of lower links versus the upper links. Each link may have an outer side, which is shown with transverse ridges and grooves, and an opposite inner side. The outer sides of links 402, 404, 406, 408 are shown in FIG. 8A; the outer sides of links 412, 414, 416, 418 are shown in FIG. 8B. The upper link 402 may include a post 420 that protrudes from the inner side near one end, and a through hole 422 that extends through the outer and inner sides near the opposite end. The upper link 404 may include a through hole 424 that extends through the outer and inner sides near one end, and a post 426 that protrudes from the inner side near the opposite end. The upper link 406 may include a through hole 428 that extends through the outer and inner sides near one end. The inner side at the opposite end may be featureless as shown, or it may optionally include a hole (not shown). The upper link 408 may include a post 430 that protrudes from the inner side near one end, and a snap boss 432 that protrudes from the outer side near the opposite end. The lower link 412 may include a through hole 434 that extends through the outer and inner sides near one end, and a post 436 that protrudes from the inner side near the opposite end. The post 436 may include a longitudinal through hole 438. The lower link 414 may include a post 440 that protrudes from the inner side near one end. The post 440 may include a longitudinal through hole 442. A through hole 444 may extend through the outer and inner sides near the opposite end. The lower link 416 may include a post 446 that protrudes from the inner side near one end. The post 446 may include a longitudinal through hole 448. A snap boss 450 may protrude from the outer side near the opposite end. The lower link 418 may include a through hole 452 that extends through the outer and inner sides near one end. The inner side at the opposite end may be featureless as shown, or it may optionally include a hole (not shown).

The post 440 of the lower link 414 may be received in the through hole 434 of the lower link 412 and the through hole 424 of the upper link 404, and the post 420 of the upper link 402 may be received in the hole 442 of the lower link 414. The post 446 of the lower link 416 may be received in the through hole 444 of the lower link 414 and the through hole 428 of the upper link 406, and the post 426 of the upper link 404 may be received in the hole 448 of the lower link 416. The post 436 of the lower link 412 may be received in the through hole 452 of the lower link 418 and the through hole 422 of the upper link 402, and the post 430 of the upper link 408 may be received in the hole 438 of the lower link 412. The snap boss 432 of the 408 may be received in the optional hole (if present) of the 406. The snap boss 450 of the 416 may be received in the optional hole (if present) of the 418. These connections may hinge the links together to enable lateral expansion. The connections may permit the through holes 422, 424, 428 to slide along the posts 436, 440, 446, respectively, to enable vertical expansion. The connections may permit the posts 420, 426, 430 to slide within the holes 442, 448, 438, respectively, to enable vertical expansion.

The wedge 500, or spreading clip, may include a leading end 502 and a trailing end 504. The trailing end 504 may support right and left prongs 506, 508 which extend to the leading end 502. Each prong may taper down in height towards the leading end 502. Each prong may include a snap feature to engage with the fusion cage 400. Snap features 514, 516 are illustrated as vertically extending ridges on the inner sides of the prongs 506, 508. The snap features may be located toward the leading end 502 to engage with the post 440 or the boss surrounding the hole 424. A gap 510 may separate the prongs. A longitudinal hole 512 may extend through the trailing end along a direction between the leading and trailing ends.

The fusion cage 400 may be expanded laterally by coupling it to an instrument (not shown) and actuating the instrument to draw the post 420, hole 424, hole 434, and post 440 (the leading end) toward the snap boss 432 (the trailing end) and urge the hole 422, post 430, post 436, and hole 452 away from the post 426, hole 428, hole 444, and post 446. The instrument may abut the trailing end and may extend between the upper and lower quadrilaterals to engage the leading end. The instrument may grasp the post 440 (for example) with a pair of jaws, or may partially or fully encircle the post 440 or the boss surrounding the hole 424.

The fusion cage 400 may be expanded vertically by an instrument (not shown) which is actuated to urge the upper links away from the lower links. Separate instruments may be used for lateral and vertical expansion, or one instrument may be used for both lateral and vertical expansion. Alternatively, the fusion cage may be laterally and/or vertically expanded by the wedge 500.

The wedge 500 may lock the fusion cage 400 in its laterally and/or vertically expanded configuration. The illustrated embodiment shows a wedge that locks the fusion cage vertically by filling the gap between the upper and lower quadrilaterals. The wedge 500 may be modified to also lock the fusion cage laterally. Referring to FIGS. 7B, 7C, 8A, and 8B, in one example the leading end of the prong 506 may include a lower augmentation that fills the gap between the lower links 412, 414; the trailing end of the prong 506 may include an upper augmentation that fills the gap between the upper links 406, the 408; the leading end of the prong 508 may include an upper augmentation that fills the gap between the upper links 402, 404; and the trailing end of the prong 508 may include a lower augmentation that fills the gap between the lower links 416, 418. A single one of these four augmentations may be sufficient to lock the fusion cage laterally.

The wedge 500 may connect to the expanded fusion cage 400 via the snap features 514, 516, as described above. An optional locking screw (not shown) may be inserted through the hole 512 and into a hole (not shown) in the post 440 or the boss surrounding the hole 424.

Figure 9A:
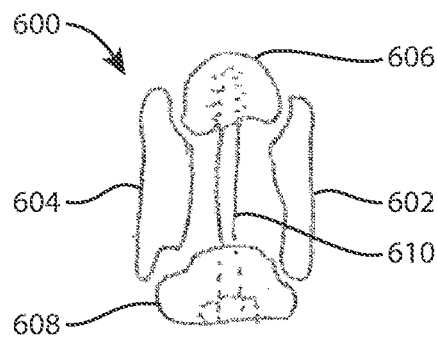
FIG. 9A is a hand sketch of yet another expanding fusion cage.
Figure 9A:
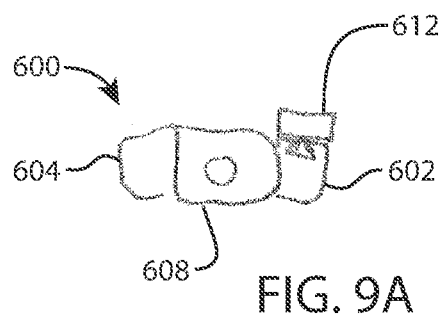
Figure 9B:
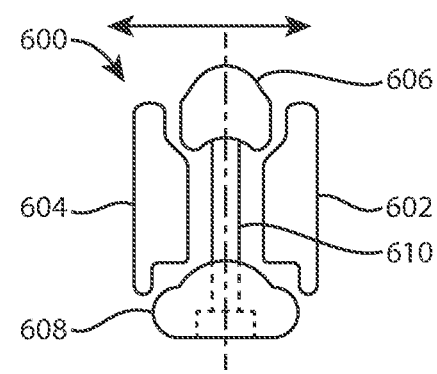
FIG. 9B is a schematic drawing of the fusion cage of the hand sketch of FIG. 9A.
Figure 9B:
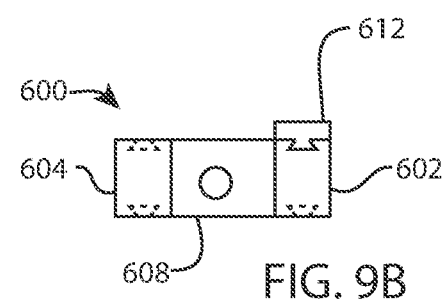

Referring to FIGS. 9A and 9B, another expanding fusion cage 600 is shown. Fusion cage 600 expands laterally via a screw drive and linkages. The horizontal line with arrowhead ends indicates the lateral direction. The linkages are not shown. Fusion cage 600 is expanded vertically via the addition of struts. The leading and trailing components 606 and 608 are brought together via a screw 610, which causes the left and right lateral components 604 and 602 to expand out laterally. Vertical expansion is achieved via the addition of one or more struts, such as strut 612. These struts can be added to any or all locations to achieve proper anatomic fit. The struts may be connected to the components 604, 602, 606, or 608 via dovetails. Note the presence of some optional additional dovetail channels in dashed lines in FIG. 9B.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. An expandable fusion cage system comprising:
a cage comprising a plurality of links hinged together end to end, wherein the links are rotatable relative to each other in a plane;
a wedge component having a tapered first end; and
wherein each one of the plurality of links comprises an upper member and a lower member, wherein the upper members are movable relative to the lower members along an axis normal to the plane; and
wherein the wedge component is receivable between the upper and lower members;
wherein the plurality of links further comprises:
a first link extending from a first end to a second end having a first upper member and a first lower member;
a second link extending from a first end to a second end having a second upper member and a second lower member;
a third link extending from a first end to a second end having a third upper member and a third lower member;
a fourth link extending from a first end to a second end having a fourth upper member and a fourth lower member; and
wherein the first link is connected to the second link at the respective first ends, which are connected via a first post;
wherein the first link is connected to the third link at the respective second ends, which are connected via a second post;
wherein the second link is connected to the fourth link at the respective second ends, which are connected via a third post;
wherein the third link is connected to the fourth link at the respective first ends, which are separated by a first distance.

2. The expandable fusion cage system of claim 1, wherein the wedge component further comprises a first and a second parallel arm each having a tapered first end, and wherein the first and second arms are joined at a second end.

3. The expandable fusion cage system of claim 1, wherein the plurality of links further comprises four links hinged together to form a quadrilateral polygon.

4. The expandable fusion system of claim 1, wherein the wedge component further comprises a first and a second parallel arm each having a tapered first end, wherein the first and second arms are joined at a second end; and
wherein the wedge is insertable between the upper and lower members of the first and second links, so that first post is between the first and second arms of the wedge, and when the wedge is inserted farther past the first post, the upper and lower members of the first and second links are moved from a first insertion distance to a second expanded distance.

5. The expandable fusion system of claim 1, wherein the second end of the wedge component has a concave curvature that is complimentary to a curvature of one of the first post, second post, or the third post.

6. The expandable fusion system of claim 1, wherein the cage is transformable from a first insertion height to a second expanded height, by the insertion of the tapered ends of the wedge component between any of the upper and lower members.

7. The expandable fusion system of claim 1, wherein the cage is transformable from a first insertion width to a second expanded width, by the insertion of the tapered ends of the wedge component between any of the upper and lower members of the cage.

8. The expandable fusion system of claim 7, wherein when the wedge component is inserted into the cage, the first and second arms cause the second post and the third post to move away from one another.

9. The expandable fusion system of claim 8, wherein when the wedge component is inserted into the cage, the first and second arms cause the first ends of the first and second links to move closer to the first ends of the third and fourth links.

10. An expandable fusion cage system comprising:
    a cage comprising a plurality of links hinged together end to end, wherein the links are rotatable relative to each other in a plane, wherein the plurality of links comprises four links hinged together to form a quadrilateral polygon;
    a wedge component having a tapered first end; and
    wherein each one of the plurality of links comprises an upper member and a lower member, wherein the upper members are movable relative to the lower members along an axis normal to the plane; and
    wherein the wedge component is receivable between the upper and lower members.

11. The expandable fusion cage system of claim 10, wherein the wedge component further comprises a first and a second parallel arm each having a tapered first end, and wherein the first and second arms are joined at a second end.

12. The expandable fusion cage of claim 10, wherein the plurality of links further comprises:
    a first link extending from a first end to a second end having a first upper member and a first lower member;
    a second link extending from a first end to a second end having a second upper member and a second lower member;
    a third link extending from a first end to a second end having a third upper member and a third lower member;
    a fourth link extending from a first end to a second end having a fourth upper member and a fourth lower member; and
    wherein the first link is connected to the second link at the respective first ends, which are connected via a first post;
    wherein the first link is connected to the third link at the respective second ends, which are connected via a second post;
    wherein the second link is connected to the fourth link at the respective second ends, which are connected via a third post;
    wherein the third link is connected to the fourth link at the respective first ends, which are separated by a first distance.

13. The expandable fusion system of claim 12, wherein the wedge component further comprises a first and a second parallel arm each having a tapered first end, wherein the first and second arms are joined at a second end; and
    wherein the wedge is insertable between the upper and lower members of the first and second links, so that first post is between the first and second arms of the wedge, and when the wedge is inserted farther past the first post, the upper and lower members of the first and second links are moved from a first insertion distance to a second expanded distance.

14. The expandable fusion system of claim 12, wherein the second end of the wedge component has a concave curvature that is complimentary to a curvature of one of the first post, second post, or the third post.

15. The expandable fusion system of claim 12, wherein the cage is transformable from a first insertion height to a second expanded height, by the insertion of the tapered ends of the wedge component between any of the upper and lower members.

16. The expandable fusion system of claim 12, wherein the cage is transformable from a first insertion width to a second expanded width, by the insertion of the tapered ends of the wedge component between any of the upper and lower members of the cage.

17. The expandable fusion system of claim 16, wherein when the wedge component is inserted into the cage, the first and second arms cause the second post and the third post to move away from one another.

18. The expandable fusion system of claim 17, wherein when the wedge component is inserted into the cage, the first and second arms cause the first ends of the first and second links to move closer to the first ends of the third and fourth links.

* * * * *